(12) United States Patent
Kozian et al.

(10) Patent No.: US 7,985,562 B2
(45) Date of Patent: Jul. 26, 2011

(54) METHOD FOR THE IDENTIFICATION OF A RISK FOR A THROMBOGENIC DISORDER BY DETERMINING THE TAFI-LLE347 POLYMORPHISM

(75) Inventors: Detlef Kozian, Kelkheim (DE); Stefan Schaefer, Liederbach (DE); Bernward Schoelkens, Kelkheim (DE); Karl-Ernst Siegler, Ludwigshafen (DE); Jean-Francois Deleuze, Combs la Ville (FR); Sylvain Ricard, Paris (FR); Sandrine Mace, Jouy-En-Josas (FR)

(73) Assignee: Sanofi-Aventis Deutsckland GmbH, Frankfurt am Main (DE)

( * ) Notice: Subject to any disclaimer, the term of this patent is extended or adjusted under 35 U.S.C. 154(b) by 0 days.

(21) Appl. No.: 12/474,794

(22) Filed: May 29, 2009

(65) Prior Publication Data

US 2009/0239237 A1   Sep. 24, 2009

Related U.S. Application Data

(62) Division of application No. 11/184,010, filed on Apr. 1, 2004, now Pat. No. 7,560,290.

(30) Foreign Application Priority Data

Nov. 12, 2003 (EP) .................................... 03026030

(51) Int. Cl.
*G01N 33/00* (2006.01)
(52) U.S. Cl. ........ 435/7.92; 435/7.9; 435/115; 435/116; 436/86; 436/501
(58) Field of Classification Search .................. None
See application file for complete search history.

(56) References Cited

U.S. PATENT DOCUMENTS

| 5,593,674 | A | 1/1997 | Drayna et al. |
| 5,747,305 | A | 5/1998 | Jackson |
| 5,985,562 | A | 11/1999 | Morser et al. |
| 2005/0032703 | A1* | 2/2005 | Greenfield et al. .............. 514/12 |

OTHER PUBLICATIONS

Boffa et al., Characterization of the Gene Encoding Human TAFI (Thrombin-Activable Fibrinolysis Inhibitor; Plasma Procarboxypeptidase B), Biochemistry, 1999, vol. 38, pp. 6547-6558.
Boffa et al., Thrombin Activable Fibrinolysis Inhibitor (TAFI): Molecular Genetics Of An Emerging Potential Risk Factor For Thrombotic Disorders, Current Drug Targets, Bentham Science Publ., 2001, vol. 1, No. 2, pp. 59-74.
Brouvers et al., A novel, possibly functional, single nucleotide polymorphism in the coding region of the thrombin-activatable fibrinolysis inhibitor (TAFI) gene is also associated with TAFl leveis, Blood, Sep. 15, 2001, vol. 98, No. 6, pp. 1992-1993.
Franco et al., Identification of polymorphisms in the 5'-untranslated region of the TAFI gene: relationship with plasmaTAFI levels and risk of venous thrombosis, Haematologica, 2001, vol. 86, pp. 510-517.
Henry et al., Identification of polymorphisms in the promoterand the 3' region of the TAFI gene: evidence that plasma TAFI antigen levels are strongly genetically controlled, Blood, Apr. 1, 2001, vol. 27, No. 7, pp. 2053-2058.
Montaner et al., Thrombin-Activable Fibrinolysis Inhibitor Levels in The Acute Phase of Ischemic Stroke, Stroke, American Heart Assn., Apr. 2003, vol. 34, No. 4, pp. 1038-1040.
Santamaria et al., Risk of Ischemic Stroke Associated With Functional Thrombin-Activatable Fibrinolysis Inhibitor Plasma Levels, Stroke, American Heart Assn. , Oct. 2003, vol. 34, No. 10, pp. 2387-2391.
Schneider et al., Two naturally occurring variants of TAFI (Thr-325 and lle-325) differ substantially with respect to thermal stability and antifibrinolytic activity of the enzyme, J. of Biol. Chem., Jan. 11, 2002, vol. 277, No. 2, pp. 1021-1030.
Van Theil et al., Low Levels of Thrombin Activatable Fibrinolysis Inhibitor (TAFI) in Patients With Chronic Liver Disease, Thrombosis and Haemostasis,Apr. 2001, vol. 85, No. 4, pp. 667-670.
Zorio et al., Thrombin-activable fibrinolysis inhibitor in young patients with myocardial infarction and its relationship with the fibrinolylic functin and the protein C system, Brit. Journal of Haematology, Sep. 2003, vol. 122, No. 6, pp. 956-965.

* cited by examiner

Primary Examiner — Melanie J Yu
Assistant Examiner — Gary Counts

(57) ABSTRACT

The present invention is directed to a method identifying a risk for a thrombogenic disorder, to a method for selecting patients with a risk for a thrombogenic disorder, to a method for identifying a pharmaceutical for the therapy or prophylaxis of a thrombogenic disorder as well as to a method for producing a medicament and a diagnostic by employing the TAFI-Ile347 polymorphism.

9 Claims, 2 Drawing Sheets

SEQ ID NO: 1

SEQ ID NO: 2

```
   1 GTTGTACAGA AAAATTGCTGT TGGGATGAAG CTTTGCAGCC TTGCAGTCCT TGTACCCATT
  61 GTTCTCTTCT GTGAGCAGCA TGTCTTCGCG TTTCAGAGTG GCCAAGTTCT AGCTGCTCTT
 121 CCTAGAACCT CTAGGCAAGT TCAAGTTCTA CAGAATCTTA CTACAACATA TGAGATTGTT
 181 CTCTGGCAGC CGGTAACAGC TGACCTTATT GTGAAGAAAA AACAAGTCCA TTTTTTTGTA
 241 AATGCATCTG ATGTCGACAA TGTGAAAGCC CATTTAAATG TGAGCGGAAT TCCATGCAGT
 301 GTCTTGCTGG CAGACGTGGA AGATCTTATT CAACAGCAGA TTTCCAACGA CACAGTCAGC
 361 CCCCGAGCCT CCGCATCGTA CTATGAACAG TATCACTCAC TAAATGAAAT CTATTCTTGG
 421 ATAGAATTTA TAACTGAGAG GCATCCTGAT ATGCTTACAA AAATCCACAT TGGATCCTCA
 481 TTTGAGAAGT ACCCACTCTA TGTTTTAAAG GTTTCTGGAA AAGAACAAAC AGCCAAAAAT
 541 GCCATATGGA TTGACTGTGG AATCCATGCC AGAGAATGGA TCTCTCCTGC TTTCTGCTTG
 601 TGGTTCATAG GCCATATAAC TCAATTCTAT GGGATAATAG GGCAATATAC CAATCTCCTG
 661 AGGCTTGTGG ATTTCTATGT TATGCCGGTG GTTAATGTGG ACGGTTATGA CTACTCATGG
 721 AAAAAGAATC GAATGTGGAG AAAGAACCGT TCTTTCTATG CGAACAATCA TTGCATCGGA
 781 ACAGACCTGA ATAGGAACTT TGCTTCCAAA CACTGGTGTG AGGAAGGTGC ATCCAGTTCC
 841 TCATGCTCGG AAACCTACTG TGGACTTTAT CCTGAGTCAG AACCAGAAGT GAAGGCAGTG
 901 GCTAGTTTCT TGAGAAGAAA TATCAACCAG ATTAAAGCAT ACATCAGCAT GCATTCATAC
 961 TCCCAGCATA TAGTGTTTCC ATATTCCTAT ACACGAAGTA AAAGCAAAGA CCATGAGGAA
1021 CTGTCTCTAG TAGCCAGTGA AGCAGTTCGT GCTATTGAGA AAACTAGTAA AAATACCAGG
1081 TATACACATG GCCATGGCTC AGAAACCTTA TACCTAGCTC CTGGAGGTGG GGACGATTGG
1141 ATCTATGATT TGGGCATCAA ATATTCGTTT ACAATTGAAC TTCGAGATAC GGGCACATAC
1201 GGATTCTTGC TGCCGGAGCG TTACATCAAA CCCACCTGTA GAGAAGCTTT TGCCGCTGTC
1261 TCTAAAATAG CTTGGCATGT CATTAGGAAT GTTTAATGCC CCTGATTTTA TCATTCTGCT
1321 TCCGTATTTT AATTTACTGA TTCCAGCAAG ACCAAATCAT TGTATCAGAT TATTTTTAAG
1381 TTTTATCCGT AGTTTTGATA AAAGATTTTC CTATTCCTTG GTTCTGTCAG AGAACCTAAT
1441 AAGTGCTACT TTGCCATTAA GGCAGACTAG GGTTCATGTC TTTTTACCCT TTAAAAAAAA
1501 TTGTAAAAGT CTAGTTACCT ACTTTTTCTT TGATTTTCGA CGTTTGACTA GCCATCTCAA
1561 GCAACTTTCG ACGTTTGACT AGCCATCTCA AGCAAGTTTA ATCAAAGATC ATCTCACGCT
1621 GATCATTGGA TCCTACTCAA CAAAAGGAAG GGTGGTCAGA AGTACATTAA AGATTTCTGC
1681 TCCAAATTTT CAATAAATTT CTGCTTGTGC CTTTAGAAAT ACA
```

Figure 2

METHOD FOR THE IDENTIFICATION OF A RISK FOR A THROMBOGENIC DISORDER BY DETERMINING THE TAFI-LLE347 POLYMORPHISM

CROSS-REFERENCE TO RELATED APPLICATIONS

This patent application is a divisional of U.S. patent application Ser. No. 11/184,010 filed Apr. 1, 2004, now U.S. Pat. No. 7,560,290 issued Jul. 14, 2009, which claims priority to EP03026030.1 filed Nov. 12, 2003, which are incorporated herein by reference in their entireties.

BACKGROUND OF THE INVENTION

The present invention is directed to a method identifying a risk for a thrombogenic disorder including, without limitation, atrial fibrillation, stroke, prolonged intermitted neurological deficit (PRIND), transitory ischemic attack (TIA), atherosclerotic cerebrovascular disease (CVD) and/or coronary heart disease, as well as to a method for selecting patients with a risk for a thrombogenic disorder, to a method for identifying a pharmaceutical for the therapy or prophylaxis of a thrombogenic disorder as well as to a method for producing a medicament and a diagnostic by employing the TAFI-Ile347 polymorphism.

The Thrombin-Activable Fibrinolysis Inhibitor (TAFI) is a known plasma zymogen synthesized in the liver as a pre-propeptide consisting of 423 amino acids with a molecular weight of 55 kDa (FIG. 1). The prepropeptide contains a 22 amino acids long signal peptide (amino acids No. 1-22), a 92 amino acids long activation peptide and a 309 amino acids long catalytic domain. The nucleic acid sequence contains 1723 nucleotides (FIG. 2). The protein sequence accession number (NCBI protein database) of TAFI is NP_001863, the nucleotide sequence accession number (NCBI nucleotide database) is NM_001872 and the accession number for TAFI information in OMIM (Online Mendelian Inheritance in Man™) is 603101.

TAFI is activated by thrombin, plasmin or the thrombin/thrombomodulin complex. After processing, TAFI attenuates clot lysis by removing lysine residues from a fibrin clot. Activated and processed TAFI is unstable at 37° C. and has a half-life of about 8 minutes. Therefore, TAFI plays a central role in homeostasis where it functions as a potent fibrinolysis inhibitor. The human TAFI gene has been mapped to chromosome 13q14.11. It consists of 11 exons and spans a genomic region of about 48 kb in length (Boffa et al. (1999) Biochemistry, 38, 6547-6558).

Genetic analyses of the TAFI gene in humans revealed several variable nucleotides (SNPs, Single Nucleotide Polymorphisms) in the promoter and the coding region. For SNPs in the promoter region of the TAFI gene it has been shown, that some of these polymorphisms are associated with altered TAFI protein levels in the blood (Franco et al. (2001) Haematologica, 86, 510-517; Henry et al. (2001) Blood, vol. 97, no. 7, 2053-2058).

Recently two SNPs have been identified in the coding region of the TAFI gene leading to an amino acid exchange in the corresponding TAFI protein, these polymorphism are T169A (T=Threonine (Thr) at position 169 to A=Alanine (Ala)) and T347I (Threonine at position 347 to I=Isoleucine (Ile)). The TAFI-Ile347 variant seems to display an extended half-life from 8 minutes to 15 minutes and seems to exhibit an enhanced antifibrinolytic potential of 60% (Brouwers et al. (2001) Blood, vol. 98, no. 6, 1992-1993; Schneider et al. (2001) J. Biological Chemistry, vol. 277, no. 2, 1021-1030) under the tested in vitro conditions. Variations at position 169 of the TAFI protein do not seem to have any effect on the antifibrinolytic potential of TAFI (Schneider et al. (2001) supra). However, currently no data are available about the clinical effects, if any, of the described polymorphisms including the TAFI-Ile347 variant for thrombogenic or other disorders.

BRIEF DESCRIPTION OF THE DRAWINGS

FIG. 1 shows the protein sequence of TAFI (SEQ ID NO: 1).

FIG. 2 shows the nucleotide sequence of TAFI (SEQ ID NO: 2).

DETAILED DESCRIPTION OF THE INVENTION

According to the present invention it has been found that in particular individuals with a TAFI-Ile347 polymorphism have an increased risk for stroke and transitory ischemic attack (TIA). Therefore, the genetic TAFI-Ile347 polymorphism can be used as a genetic marker, e.g. for the identification of a risk for a thrombogenic disorder, for the selection of patients with a risk for a thrombogenic disorder, e.g. in clinical studies, for the identification of a pharmaceutical for the therapy and/or prophylaxis of a thrombogenic disorder, for the production of a medicament for the preventive and/or therapeutic treatment of a thrombogenic disorder, for the production of a diagnostic for the identification of a thrombogenic disorder and/or for the adaptation of the dosage of a medicament for the treatment and/or prophylaxis of a thrombogenic disorder.

Therefore, one embodiment of the present invention is directed to an in vitro or in vivo method for identifying a risk for a thrombogenic disorder including, without limitation, the risk for an atrial fibrillation, stroke, prolonged intermitted neurological deficit (PRIND), transitory ischemic attack (TIA) and, atherosclerotic cerebrovascular disease (CVD) and/or coronary heart disease, wherein the method comprises determining in a sample the presence of an amino acid exchange from threonine to isoleucine at position 347 of the Thrombin-Activable Fibrinolysis Inhibitor (TAFI) with the amino acid sequence according to SEQ ID NO: 1 (TAFI-Ile347). Because diabetics often show hypofibrinolysis the sample is preferably from a diabetic. Generally, the sample is a cell or a body fluid, e.g. blood or an animal or a human cell, isolated from an animal or human body.

TIA, PRIND and stroke are neurological deficits with a sudden onset due to a vascular disease such as a thrombogenic disorder which differs only in the time period of reconvalescence and in the severity. For example, for TIA the neurologic deficits generally last less than 24 hours and no permanent brain damage results. For PRIND the neurologic deficits generally last for more than 24 hours without permanent brain damages. A stroke generally results in a permanent brain damage.

The TAFI-Ile347 polymorphism can be generally determined by methods known to a person skilled in the art. One method is to determine the amino acid exchange by amino acid sequencing, e.g. standard protein degradation or analysis of protein sequence fragments with mass spectrometry, enzymatic treatment of the protein and subsequent analysis of degradation products or by means of a binding protein or a binding peptide or aptamer, specifically directed against TAFI-Ile347, in particular by means of an antibody, an antigen-binding part of an antibody and/or a protein-scaffold, preferably an anticalin.

According to the present invention the term "binding protein" or "binding peptide" refers to a class of proteins or peptides which specifically bind TAFI or TAFI-Ile347 including, without limitation, monospecific polyclonal or monoclonal antibodies, antibody fragments and protein scaffolds specifically directed against TAFI or TAFI-Ile347, e.g. anticalins which are specifically directed against TAFI-Ile347. The term "specifically" means that the binding protein or binding peptide discriminates between TAFI-Ile347 and other polymorphisms at amino acid position No. 347 of TAFI, in particular TAFI-Thr347.

The determination of other polymorphisms at amino acid position No. 347 of TAFI, in particular TAFI-Thr347 may be used as a reference or control in the method of the present invention.

The procedure for preparing an antibody or antibody fragment is effected in accordance with methods which are well known to the skilled person, e.g. by immunizing a mammal, for example a rabbit, with TAFI or TAFI-Ile347, where appropriate in the presence of, for example, Freund's adjuvant and/or aluminium hydroxide gels (see, for example, Diamond, B. A. et al. (1981) The New England Journal of Medicine: 1344-1349). The polyclonal antibodies which are formed in the animal as a result of an immunological reaction can subsequently be isolated from the blood using well known methods and, for example, purified by means of column chromatography. Monoclonal antibodies can, for example, be prepared in accordance with the known method of Winter & Milstein (Winter, G. & Milstein, C. (1991) Nature, 349, 293-299).

According to the present invention the term "antibody" or "antibody fragment" is also understood as meaning antibodies or antigen-binding parts thereof, which have been prepared recombinantly and, where appropriate, modified, such as chimeric antibodies, humanized antibodies, multifunctional antibodies, bispecific or oligospecific antibodies, single-stranded antibodies and F(ab) or F(ab)$_2$ fragments (see, for example, EP-B1-0 368 684, U.S. Pat. No. 4,816,567, U.S. Pat. No. 4,816,397, WO 88/01649, WO 93/06213 or WO 98/24884).

As an alternative to the classical antibodies it is also possible, for example, to use protein scaffolds against TAFI or TAFI-Ile347, e.g. anticalins which are based on lipocalin (Beste et al. (1999) Proc. Natl. Acad. Sci. USA, 96, 1898-1903). The natural ligand-binding sites of the lipocalins, for example the retinol-binding protein or the bilin-binding protein, can be altered, for example by means of a "combinatorial protein design" approach, in such a way that they bind to selected haptens, here to TAFI or TAFI-Ile347 (Skerra, 2000, Biochim. Biophys. Acta, 1482, 337-50). Other known protein scaffolds are known as being alternatives to antibodies for molecular recognition (Skerra (2000) J. Mol. Recognit., 13, 167-187).

Aptamers are nucleic acids which bind with high affinity to a polypeptide, here TAFI or TAFI-ILe347. Aptamers can be isolated by selection methods such as SELEX (see e.g. Jayasena (1999) Clin. Chem., 45, 1628-50; Klug and Famulok (1994) M. Mol. Biol. Rep., 20, 97-107; U.S. Pat. No. 5,582,981) from a large pool of different single-stranded RNA molecules. Aptamers can also be synthesized and selected in their mirror-image form, for example as the L-ribonucleotide (Nolte et al. (1996) Nat. Biotechnol., 14, 1116-9; Klussmann et al. (1996) Nat. Biotechnol., 14, 1112-5). Forms which have been isolated in this way enjoy the advantage that they are not degraded by naturally occurring ribonucleases and, therefore, possess greater stability.

Another method to determine the TAFI-Ile347 polymorphism is the analysis of the TAFI gene, in particular the nucleic acid sequence at position 1064 for the detection of the nucleotide exchange from cytidine to thymidine. In general, the determination of the nucleotide exchange can be carried out by nucleic acid sequencing, e.g. pyrosequencing, sequencing methods using radio-labelled nucleotides or nucleotides labelled with a fluorescent dye, primer extension assay, analysis of sequence fragments with mass spectrometry, or by means of an antibody, an antigen-binding part of an antibody or a protein-scaffold, preferably an anticalin and/or a complementary nucleic acid, specifically directed against the mutation in the TAFI gene.

In this respect the term "specifically" means that the antibody, an antigen-binding part of an antibody or a protein-scaffold, preferably an anticalin, and/or a complementary nucleic acid discriminates between the TAFI-Ile347 gene and other polymorphisms of the nucleotide codon for amino acid position No. 347 of TAFI, in particular TAFI-Thr347. The preferred nucleotide exchange for the polymorphism of the amino acid at position No. 347 is the nucleotide at position 1064.

The complementary nucleic acids, which are preferably single stranded DNA molecules, can be synthesized chemically, e.g. in accordance with the phosphotriester method (see, for example, Uhlmann, E. & Peyman, A. (1990) Chemical Reviews, 90, 543-584). These complementary nucleic acids can be used as hybridization probes, e.g. on DNA microarrays, or as amplification probes, e.g. in the TaqMan® analysis (Taqman® Laboratory) which is a fluorogenic 5' nuclease assay.

The antibody, antigen-binding part of an antibody or the protein-scaffold can be produced accordingly as described above.

In any case it is advantageous for the method of the present invention to additionally determine other potential polymorphisms at amino acid position 347 of TAFI, e.g. TAFI-Thr347, as a reference or control preferably with a method as described above.

Generally, with the method of the present invention an increased risk for a vascular disorder including, without limitation, atrial fibrillation, stroke, prolonged intermitted neurological deficit (PRIND), transitory ischemic attack (TIA), atherosclerotic cerebrovascular disease (CVD) and/or coronary heart disease compared to a reference or control can be identified which may lead to a prophylactic and/or therapeutic treatment of an individual, e.g. a diabetic, or to the adaptation of the dosage of a pharmaceutical to be administered as described further below.

Therefore, another embodiment of the present invention is an in vitro or in vivo method for selecting patients with a risk for a thrombogenic disorder including, without limitation, the risk for an atrial fibrillation, stroke, prolonged intermitted neurological deficit (PRIND), transitory ischemic attack (TIA), atherosclerotic cerebrovascular disease (CVD) and/or coronary heart disease, wherein the method comprises determining in a sample, preferably from a diabetic, the presence of an amino acid exchange from threonine to isoleucine at position 347 of the Thrombin-Activable Fibrinolysis Inhibitor (TAFI) with the amino acid sequence according to SEQ ID NO: 1.

The present method for selecting patients with a risk for a vascular disorder is characterized and can be carried out in the same way as the method for identifying a risk for a vascular disorder described above.

Another embodiment of the present invention is directed to a method for identifying a pharmaceutical, preferably an inhibitor of TAFI-Ile347, for the therapy and/or prophylaxis of a thrombogenic disorder including, without limitation, an atrial fibrillation, stroke, prolonged intermittent neurological deficit (PRIND), transitory ischemic attack (TIA) and, atherosclerotic cerebrovascular disease (CVD) and/or coronary heart disease, wherein the method comprises the steps of:
(a) providing TAFI-Ile347 or the TAFI-Ile347 gene,
(b) providing a test compound, and
(c) measuring or detecting the influence of the test compound on TAFI-Ile347 or the TAFI-Ile347 gene.

According to the present invention the term "inhibitor" refers to a biochemical or chemical compound which inhibits or reduces the zymogenic activity of TAFI-Ile347, in particular the removal of lysine residues from a fibrin clot, and/or reduces the half-life of TAFI-Ile347, especially by at least about 20% to about 50%, preferably at least by about 30% to about 45%, in particular by about 45%. The term "about" means generally an error range of +/−20%, especially +/−10%, preferably +/−5%.

In general, TAFI-Ile347 or the TAFI-Ile347 gene is provided e.g. in an assay system and brought directly or indirectly into contact with a test compound, in particular a biochemical or chemical test compound, e.g. in the form of a chemical compound library. Then, the influence of the test compound on TAFI-Ile347 or the TAFI-Ile347 gene is measured or detected. Thereafter, suitable inhibitors can be analyzed and/or isolated. For the screening of chemical compound libraries, the use of high-throughput assays are preferred which are known to the skilled person or which are commercially available.

According to the present invention the term "chemical compound library" refers to a plurality of chemical compounds that have been assembled from any of multiple sources, including chemically synthesized molecules and natural products, or that have been generated by combinatorial chemistry techniques.

In general, the influence of the test compound on TAFI-Ile347 or the TAFI-Ile347 gene is measured or detected in a heterogeneous or homogeneous assay. As used herein, a heterogeneous assay is an assay which includes one or more washing steps, whereas in a homogeneous assay such washing steps are not necessary. The reagents and compounds are only mixed and measured.

Suitable functional assays may be based on the gene expression of TAFI-Ile347. In the presence of a biochemical or chemical compound to be tested as an inhibitor of TAFI-Ile347 gene expression, the direct inhibition can be measures by means generally known to a skilled person and as described above. For example, in order to measure the enzymatic activity of TAFI (e.g. as a reference or control) and/or TAFI-Ile347 the clot lysis and/or the removal of lysin residues from fibrin or generally its carboxypeptidase activity using e.g. the synthetic carboxypeptidase substrate anisylazoformyllysine can be measured in an appropriate assay known to a person skilled in the art (see e.g. Schneider, M. et al. (2002) supra).

Heterogeneous assays are, for example, ELISA (enzyme linked immuno sorbent assay), DELFIA, SPA and flashplate assays.

ELISA is a generally known assay which uses an enzyme as the marker molecule, e.g. a peroxidase colour reaction is initiated by addition of the peroxidase substrate and the optical density is measured in a suitable densitometer.

DELFIA (dissociation enhanced lanthanide fluoro immuno assay)-based assays are solid phase assay. The antibody is usually labelled with Europium or another lanthanide and the Europium fluorescence is detected after having washed away un-bound Europium-labelled antibodies.

SPA (scintillation proximity assay) and the flashplate assay usually exploit biotin/avidin interactions for capturing radiolabeled substrates. Generally the reaction mixture includes a biotinylated peptide substrate. After the reaction, the biotinylated peptides are captured by streptavidin. In the SPA detection, streptavidin is bound on scintillant containing beads whereas in the flashplate detection, streptavidin is bound to the interior of the well of scintillant containing microplates. Once immobilized, the radiolabelled substrate is close enough to the scintillant to stimulate the emission of light.

Alternative homogeneous assays are, for example, TR-FRET, FP, ALPHA, EFC and gene assays.

TR-FRET (time-resolved fluorescence resonance energy transfer)-based assays are assays which usually exploit the fluorescence resonance energy transfer between Europium and APC, a modified allophycocyanin, or other dyes with overlapping spectra such as Cy3/Cy5 or Cy5/Cy7 (Schobel, U. et al. (1999) Bioconjugate Chem. 10, 1107-1114). After excitation e.g. of Europium with light at 337 nm, the molecule fluoresces at 620 nm. But if this fluorophore is close enough to APC, the Europium will transfer its excitation energy to APC, which fluoresces at 665 nm. After the reaction, Europium-labelled-antibodies are added along with streptavidin-APC. The close proximity of the APC to the Europium fluorophore will cause a quenching of the Europium fluorescence at benefit of the APC fluorescence (FRET).

Fluorescence polarisation (FP)-based assays are assays which use polarized light to excite fluorescent substrate peptides in solution. These fluorescent peptides are free in solution and tumble, causing the emitted light to become depolarized. When the substrate peptide binds to a larger molecule, however, its tumbling rates are greatly decreased, and the emitted light remains highly polarized.

ALPHA (amplified luminescent proximity homogenous)-based assays, are assays which rely on the transfer of singlet oxygen between donor and acceptor beads brought into proximity. Upon excitation at 680 nm, photosensitisers in donor beads convert ambient oxygen to singlet-state oxygen, which diffuses up to a distance of 200 nm. Chemiluminescent groups in the acceptor beads transfer energy to fluorescent acceptors within the bead, which then emits light at approximately 600 nm.

EFC (enzyme fragment complementation)-based assays or equivalent assays can be used in particular for high-throughput screening of compounds. The EFC assay is based on an engineered β-galactosidase enzyme that consists of two fragments—the enzyme acceptor (EA) and the enzyme donor (ED). When the fragments are separated, there is no β-galactosidase activity, but when the fragments are together they associate (complement) to form active enzyme. The EFC assay utilizes an ED-analyte conjugate in which the analyte may be recognized by a specific binding protein, such as an antibody or receptor. In the absence of the specific binding protein, the ED-analyte conjugate is capable of complementing EA to form active β-galactosidase, producing a positive luminescent signal. If the ED-analyte conjugate is bound by a specific binding protein, complementation with EA is prevented, and there is no signal. If free analyte is provided (in a sample), it will compete with the ED-analyte conjugate for binding to the specific binding protein. Free analyte will release ED-analyte conjugate for complementation with EA, producing a signal dependent upon the amount of free analyte present in the sample.

An example of a gene assay is the two-hybrid system assay (Fields and Sternglanz (1994) Trends in Genetics, 10, 286-292; Colas and Brent (1998) TIBTECH, 16, 355-363). In this test, cells are transformed with expression vectors which are expressing fusion proteins consisting of the polypeptide according to the invention and a DNA-binding domain of a transcription factor such as Gal4 or LexA. The transformed cells additionally contain a reporter gene whose promoter contains binding sites for the corresponding DNA-binding domain. By transforming with another expression vector which is expressing a second fusion protein consisting of a known or unknown polypeptide and an activation domain, for example from Gal4 or herpes simplex virus VP16, the expression of the reporter gene can be greatly increased if the second fusion protein interacts with the polypeptide. Consequently this test system can be used for screening for biochemical or chemical compounds which inhibit an interaction between TAFI-Ile347 and its substrate, e.g. fibrin. In this way, it is possible to identify novel active compounds rapidly.

Another assay is based on solid phase-bound polypeptides such as TAFI-Ile347. Thus, a test compound, for example, contains a detectable marker, for example, the compound can be radioactively labelled, fluorescence-labelled or luminescence-labelled. Furthermore, compounds can be coupled to proteins which permit indirect detection, for example by means of enzymatic catalysis employing a peroxidase assay which uses a chromogenic substrate or by means of binding a detectable antibody. Another possibility is that of investigating the solid phase-bound protein complexes by means of mass spectrometry (SELDI). Changes in the conformation of e.g. TAFI-Ile347 during its activation as the result of interaction with a test substance can be detected, for example, by the change in the fluorescence of an endogenous tryptophan residue in the polypeptide.

The solid phase-bound polypeptides can also be part of an array. Methods for preparing such arrays using solid phase chemistry and photolabile protecting groups are disclosed, for example, in U.S. Pat. No. 5,744,305. These arrays can also be brought into contact with test compound or compound libraries and tested for interaction, for example binding or changing conformation.

Advantageously the method of the present invention is carried out in a robotics system e.g. including robotic plating and a robotic liquid transfer system, e.g. using microfluidics, i.e. channeled structured.

In another embodiment of the present invention, the method is carried out in form of a high-through put screening system. In such a system advantageously the screening method is automated and miniaturized, in particular it uses miniaturized wells and microfluidics controlled by a roboter.

Another embodiment of the present invention is directed to a method for producing a medicament for the preventive and/or therapeutic treatment of a thrombogenic disorder including, without limitation, an atrial fibrillation, stroke, prolonged intermitted neurological deficit (PRIND), transitory ischemic attack (TIA) and, atherosclerotic cerebrovascular disease (CVD) and/or coronary heart disease, wherein the method comprises the steps of:
(a) identifying a pharmaceutical for the therapy and/or prophylaxis of a thrombogenic disorder according to the method described above,
(b) providing an adequate amount of the pharmaceutical identified according to step (a), and
(c) formulating the pharmaceutical with one or more pharmaceutically acceptable carriers or auxiliary substances.

For the production of the medicament of the present invention the identified pharmaceutical is usually formulated with one or more pharmaceutically acceptable carriers or auxiliary substances, such as physiological buffer solution, e.g. sodium chloride solution, demineralized water, stabilizers, such as protease or nuclease inhibitors, preferably aprotinin, ε-aminocaproic acid or pepstatin A or sequestering agents such as EDTA, gel formulations, such as white vaseline, low-viscosity paraffin and/or yellow wax, etc. depending on the kind of administration.

Suitable further additives are, for example, detergents, such as, for example, Triton X-100 or sodium deoxycholate, but also polyols, such as, for example, polyethylene glycol or glycerol, sugars, such as, for example, sucrose or glucose, zwitterionic compounds, such as, for example, amino acids such as glycine or in particular taurine or betaine and/or a protein, such as, for example, bovine or human serum albumin. Detergents, polyols and/or zwitterionic compounds are preferred.

The physiological buffer solution preferably has a pH of approx. 6.0-8.0, especially a pH of approx. 6.8-7.8, in particular a pH of approx. 7.4, and/or an osmolarity of approx. 200-400 milliosmol/liter, preferably of approx. 290-310 milliosmol/liter. The pH of the medicament is in general adjusted using a suitable organic or inorganic buffer, such as, for example, preferably using a phosphate buffer, tris buffer (tris (hydroxymethyl)aminomethane), HEPES buffer ([4-(2-hydroxyethyl)piperazino]-ethanesulphonic acid) or MOPS buffer (3-morpholino-1-propanesulphonic acid). The choice of the respective buffer in general depends on the desired buffer molarity. Phosphate buffer is suitable, for example, for injection and infusion solutions.

The medicament can be administered in a conventional manner, e.g. by means of oral dosage forms, such as, for example, tablets or capsules, by means of the mucous membranes, for example the nose or the oral cavity, in the form of dispositories implanted under the skin, by means of injections, infusions or gels which contain the medicaments according to the invention. It is further possible to administer the medicament topically and locally in order to treat the particular joint disease as described above, if appropriate, in the form of liposome complexes. Furthermore, the treatment can be carried out by means of a transdermal therapeutic system (TTS), which makes possible a temporally controlled release of the medicaments. TTS are known for example, from EP 0 944 398 A1, EP 0 916 336 A1, EP 0 889 723 A1 or EP 0 852 493 A1.

Injection solutions are in general used if only relatively small amounts of a solution or suspension, for example about 1 to about 20 ml, are to be administered to the body. Infusion solutions are in general used if a larger amount of a solution or suspension, for example one or more liters, are to be administered. Since, in contrast to the infusion solution, only a few milliliters are administered in the case of injection solutions, small differences from the pH and from the osmotic pressure of the blood or the tissue fluid in the injection do not make themselves noticeable or only make themselves noticeable to an insignificant extent with respect to pain sensation. Dilution of the formulation according to the invention before use is therefore in general not necessary. In the case of the administration of relatively large amounts, however, the formulation according to the invention should be diluted briefly before administration to such an extent that an at least approximately isotonic solution is obtained. An example of an isotonic solution is a 0.9% strength sodium chloride solution. In the case of infusion, the dilution can be carried out, for example, using sterile water while the administration can be carried out, for example, via a so-called bypass.

In another embodiment the TAFI-Ile347 or the TAFI-Ile347 gene can be used for the manufacturing of a diagnostic for the identification of a vascular disease, in particular of a diabetic, including, without limitation, an atrial fibrillation, stroke, prolonged intermittent neurological deficit (PRIND), transitory ischemic attack (TIA), atherosclerotic cerebrovascular disease (CVD) and/or coronary heart disease.

For example, the TAFI-Ile347 can be used for the production of binding proteins or binding peptides or aptamers, as described above, which can be employed as diagnostic means. The TAFI-Ile347 gene can be used itself, in particular in its single stranded form, or for the production of a complementary nucleic acid, preferably a complementary single-stranded DNA, which can be employed as a hybridization and/or amplification probe, generally known by a person skilled in the art.

Another embodiment of the present invention is directed to a method for adapting the dosage of a medicament for the treatment and/or prophylaxis of a thrombogenic disorder including, without limitation, includes an atrial fibrillation, stroke, prolonged intermittent neurological deficit (PRIND), transitory ischemic attack (TIA), atherosclerotic cerebrovascular disease (CVD) and/or coronary heart disease, wherein the method comprises (a) determining in a sample, e.g. from a diabetic, the presence of an amino acid exchange from threonine to isoleucine at position 347 of the Thrombin-Activable Fibrinolysis Inhibitor (TAFI) with the amino-acid sequence according to SEQ ID NO: 1 (TAFI-Ile347), and
(b) adapting the dosage of the medicament according to the result of step (a).

As explained above, the TAFI-Ile347 shows an extended half-life and an enhanced antifibrinolytic activity in vitro and preferably an increased risk for stroke and TIA. Therefore, individuals with a TAFI-Ile347 polymorphism need e.g. a higher amount of a medicament for the treatment and/or prophylaxis of a thrombogenic disorder. In general, the dosage of a medicament should advantageously be adapted to the genetic TAFI profile of an individual or patient, in particular of individuals or patients who are homozygous for isoleucine at position 347. The determination step (a) of the present method can be carried out as explained above.

The following Examples, Table and Figures shall explain the present invention without limiting the scope of the invention.

ABBREVIATIONS

TAFI variants having threonine at position 347 of the protein as a consequence of polymorphisms at the corresponding position on both alleles of the TAFI gene are called TAFI-347-TT.

TAFI variants having threonine and isoleucine at position 347 of the protein as a consequence of a polymorphism at the corresponding position on one of both alleles of the TAFI gene are called TAFI-347-TI.

TAFI variants having isoleucine at position 347 of the protein as a consequence of polymorphisms at the corresponding position on both alleles of the TAFI gene are called TAFI-347-II.

EXAMPLES

Figure 1:
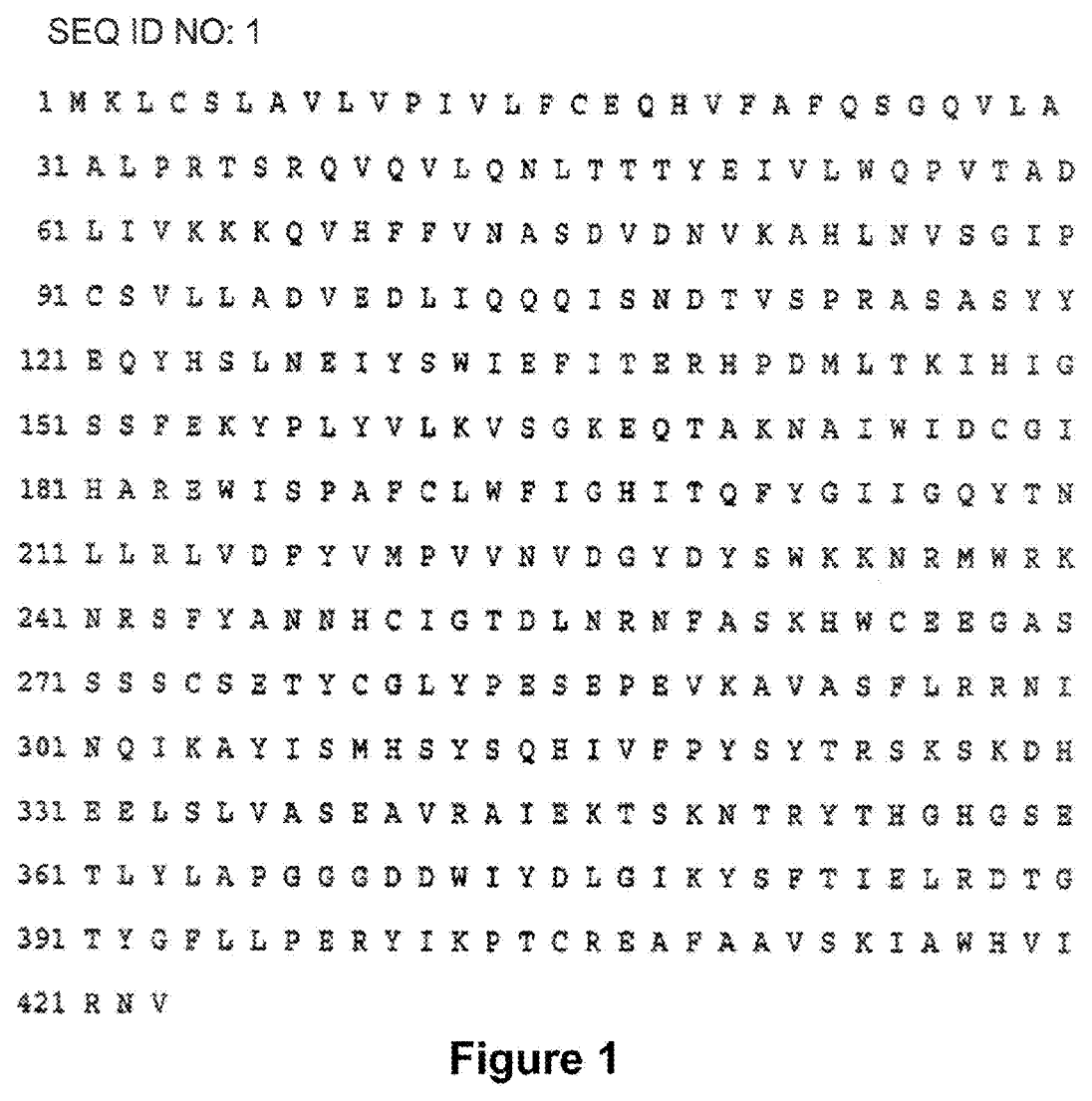

The TAFI polymorphism at the position 347 of the TAFI protein (NCBI accession number for protein sequence: NP_001863; FIG. 1) was analyzed in a patient cohort with or without cardiovascular events or endpoints.

1. SNP (Single Nucleotide Polymorphism) Detection by Sequencing and Analysis
1.1 Amplification of Genomic DNA Region with Polymorphism of Interest For the detection of the nucleotide exchange cytidine to thymidine at position 1064 of the TAFI sequence with the NCBI accession number NM_001872 leading to TAFI-Ile347 protein variant (Table 2) the following amplification primers were used:

```
Forward    5'-CACACCAGCTTTGCTACC-3'     (SEQ ID NO: 3)
primer:

Reverse    5'-CATTTTCCACTGTTTAGCTCC-3'  (SEQ ID NO: 4)
primer:
```

For the amplification the following PCR protocol was used, whereas all of the following reagents for the amplification were from Applied Biosystems (Foster City, USA): 20 ng of genomic DNA; 1 unit of TaqGold polymerase; 1×Taq polymerase buffer; 500 µM of dNTP; 2.5 mM of MgCl$_2$; 200 nM of each amplification primer pair (for sequence see Amplification primer pairs 1. above); H$_2$O ad 5 µl.

Amplification Program for PCR/Genotyping:
95° C.×10 min×1 cycle
95° C.×30 sec
70° C.×30 sec×2 cycles;
95° C.×30 sec
65° C.×30 sec×2 cycles;
95° C.×30 sec
60° C.×30 sec×2 cycles;
95° C.×30 sec
56° C.×30 sec
72° C.×30 sec×40 cycles;
72° C.×10 min
4° C.×30 sec×1 cycle;

1.2 Identification of Polymorphisms of Interest

For minisequencing and detection of polymorphisms the following protocol was used, whereas all of the following reagents were from Applied Biosystems (Foster City, USA). 2 µl of purified PCR product; 1.5 µl BigDye terminator kit; 200 nM of one sequencing primer (for sequence see forward or reverse Amplification primer 1. above); H$_2$O ad 10 µl.

Amplification Program for Sequencing:
96° C.×2'×1 cycle;
96° C.×10"
55° C.×10"
65° C.×4'×30 cycles;
72° C.×7'
4° C.×30"×1 cycle;

The sequences were analyzed first with sequencing analysis tools (Applied Biosystems, Foster City, USA) for raw data extraction, then be processed with Phred (base caller), Phrap (assembler), polyphred (SNP caller) and Consed (results viewer). Phred, Phrap, Polyphred and Consed are softwares designed at the University of Washington by Phil Green (http://www.genome.washington.edu).

1.3 Statistical Approaches for Genotype/Phenotype Correlation

All analyses were performed with SAS statistical package (Version 6.12 or higher, SAS Institute GmbH, Heidelberg/Germany). For the detection of associations between genetic polymorphisms and a large number of clinical relevant parameters, descriptive statistics were computed (median, quartiles) and Wilcoxon-rank-sum-tests were performed. Wilcoxon-rank-sum-test was used for the comparison of two independent samples. The computation of the test statistic is based on ranks in the pooled sample.

The search for associations between the SNPs and risk factors and diseases, Chi-Square-Test were performed and numbers and percentages were calculated to describe the data. The Chi-Square-Test is a statistical test for calculating the dependence of two variables. The values of the variables are contained in two or more classes. To analyze the association of those variables, a contingency table was used. This table contains as many rows as the number of realizations of the first variable and as many columns as the number of realizations of the second variable. Every cell contains a special patient's characteristic. To construct a test statistic, the differences of calculated and observed frequencies were computed.

After inspecting the results, relevant variables were selected. To take account of confounding co-variables, logistic regression was used to validate the results. The logistic regression method was used to analyze the influence of several explanatory variables on a certain response variable. The associated statistical test gave a p-value. The interpretation of this p-value is that there is a significant influence of the associated explanatory variable.

For a binary variable, the odds ratio were calculated. The odds ratio is the ratio of the odds that an event will occur in one group to the odds that the event will occur in the other group.

2. Results

The results were obtained by analyzing a subgroup of a patient population whereas the subgroup had the following characteristics: all diabetics, no treatment with the ACE inhibitor Ramipril, no alcohol.

TABLE

|  |  | TAFI 347 variants | | | | |
|---|---|---|---|---|---|---|
|  |  | II | | TT/TI | | |
|  |  | N | % | N | % | N total |
| Stroke | yes | 5 | 7.35 | 19 | 3.35 | 24 |
|  | no | 63 | 92.25 | 549 | 96.65 | 612 |
| TIA | yes | 3 | 4.41 | 4 | 0.7 | 7 |
|  | no | 65 | 95.59 | 564 | 99.3 | 629 |

As can be seen from the Table, all individuals with TAFI-I347I polymorphism have an increased risk for stroke (7.35% vs. 3.35%) and TIA (4.41% vs. 0.7%) compared to individuals with TAFI-I347T and TAFI-T347T polymorphism.

The invention claimed is:

1. A method for identifying an inhibitor of TAFI-Ile347, for the therapy or prophylaxis of a thrombogenic disorder, wherein the method comprises:
   (a) providing a TAFI-Ile347 protein or a TAFI-Ile347 gene,
   (b) contacting the TAFI-Ile347 protein or the TAFI-Ile347 gene with a test compound, and
   (c) measuring or detecting an influence of the test compound on the TAFI-Ile347 protein or the TAFI-Ile347 gene
   wherein reduction in activity of the TAFI-Ile347 protein or the TAFI-Ile347 gene identifies the test compound as said inhibitor of TAFI-Ile347 for the therapy or prophylaxis of a thrombogenic disorder.

2. The method according to claim 1, wherein the test compound is provided in the form of a chemical compound library.

3. The method according to claim 1, wherein the influence of the test compound on the TAFI-Ile347 protein or the TAFI-Ile347 gene is measured or detected in a heterogeneous or homogeneous assay.

4. The method according to claim 3, wherein the heterogeneous assay is selected from the group consisting of an ELISA (enzyme linked immuno sorbent assay), a DELFIA (dissociation enhanced lanthanide fluoro immuno assay) and an SPA (scintillation proximity assay).

5. The method according to claim 3, wherein the homogeneous assay is selected from the group consisting of a TRFRET (time-resolved fluorescence resonance energy transfer) assay, a FP (fluorescence polarization) assay, an ALPHA (amplified luminescent proximity homogenous assay), an EFC (enzyme fragment complementation) assay and a gene assay.

6. The method of claim 1, wherein the method is carried out on an array.

7. The method of claim 1, wherein the method is carried out in a robotics system.

8. The method of claim 1, wherein the method is carried out using microfluidics.

9. The method of claim 1, wherein the method is a method of high-through put screening.

* * * * *

UNITED STATES PATENT AND TRADEMARK OFFICE
CERTIFICATE OF CORRECTION

PATENT NO.        : 7,985,562 B2
APPLICATION NO.   : 12/474794
DATED             : July 26, 2011
INVENTOR(S)       : Detlef Kozian et al.

It is certified that error appears in the above-identified patent and that said Letters Patent is hereby corrected as shown below:

Title page, ITEM (54), in column 1, in "Title", line 3, delete "TAFI-LLE347" and insert -- TAFI-ILE347 --, therefor.

Title page, ITEM (73), in column 1, in "Assignee", line 1, delete "Deutsckland" and insert -- Deutschland --, therefor.

Title page, ITEM (56), in column 2, under "Other Publications", line 10, delete "TAFI leveis," and insert -- TAFI levels, --, therefor.

Title page, ITEM (56), in column 2, under "Other Publications", line 28, delete "lle-325)" and insert -- Ile-325) --, therefor.

Title page, ITEM (56), in column 2, under "Other Publications", line 31, delete "Theil" and insert -- Thiel --, therefor.

Title page, ITEM (56), in column 2, under "Other Publications", line 37, delete "956-965." and insert -- 958-965. --, therefor.

In column 1, line 3, delete "TAFI-LLE347" and insert -- TAFI-ILE347 --, therefor.

In column 8, line 14, delete "zwifterionic" and insert -- zwitterionic --, therefor.

In column 8, line 17, delete "zwifterionic" and insert -- zwitterionic --, therefor.

In column 12, line 21-22, delete "TAFI-13471" and insert -- TAFI-I347I --, therefor.

Signed and Sealed this
Eighth Day of November, 2011

David J. Kappos
*Director of the United States Patent and Trademark Office*

SEQUENCE LISTING

<160> NUMBER OF SEQ ID NOS: 4

<210> SEQ ID NO 1
<211> LENGTH: 423
<212> TYPE: PRT
<213> ORGANISM: Homo sapiens

<400> SEQUENCE: 1

```
Met Lys Leu Cys Ser Leu Ala Val Leu Val Pro Ile Val Leu Phe Cys
1               5                   10                  15

Glu Gln His Val Phe Ala Phe Gln Ser Gly Gln Val Leu Ala Ala Leu
            20                  25                  30

Pro Arg Thr Ser Arg Gln Val Gln Val Leu Gln Asn Leu Thr Thr Thr
        35                  40                  45

Tyr Glu Ile Val Leu Trp Gln Pro Val Thr Ala Asp Leu Ile Val Lys
    50                  55                  60

Lys Lys Gln Val His Phe Phe Val Asn Ala Ser Asp Val Asp Asn Val
65                  70                  75                  80

Lys Ala His Leu Asn Val Ser Gly Ile Pro Cys Ser Val Leu Leu Ala
                85                  90                  95

Asp Val Glu Asp Leu Ile Gln Gln Gln Ile Ser Asn Asp Thr Val Ser
            100                 105                 110

Pro Arg Ala Ser Ala Ser Tyr Tyr Glu Gln Tyr His Ser Leu Asn Glu
        115                 120                 125

Ile Tyr Ser Trp Ile Glu Phe Ile Thr Glu Arg His Pro Asp Met Leu
    130                 135                 140

Thr Lys Ile His Ile Gly Ser Ser Phe Glu Lys Tyr Pro Leu Tyr Val
145                 150                 155                 160

Leu Lys Val Ser Gly Lys Glu Gln Thr Ala Lys Asn Ala Ile Trp Ile
                165                 170                 175

Asp Cys Gly Ile His Ala Arg Glu Trp Ile Ser Pro Ala Phe Cys Leu
            180                 185                 190
```

```
Trp Phe Ile Gly His Ile Thr Gln Phe Tyr Gly Ile Ile Gly Gln Tyr
            195                 200                 205

Thr Asn Leu Leu Arg Leu Val Asp Phe Tyr Val Met Pro Val Val Asn
        210                 215                 220

Val Asp Gly Tyr Asp Tyr Ser Trp Lys Lys Asn Arg Met Trp Arg Lys
225                 230                 235                 240

Asn Arg Ser Phe Tyr Ala Asn Asn His Cys Ile Gly Thr Asp Leu Asn
                245                 250                 255

Arg Asn Phe Ala Ser Lys His Trp Cys Glu Glu Gly Ala Ser Ser Ser
            260                 265                 270

Ser Cys Ser Glu Thr Tyr Cys Gly Leu Tyr Pro Glu Ser Glu Pro Glu
        275                 280                 285

Val Lys Ala Val Ala Ser Phe Leu Arg Arg Asn Ile Asn Gln Ile Lys
    290                 295                 300

Ala Tyr Ile Ser Met His Ser Tyr Ser Gln His Ile Val Phe Pro Tyr
305                 310                 315                 320

Ser Tyr Thr Arg Ser Lys Ser Lys Asp His Glu Glu Leu Ser Leu Val
                325                 330                 335

Ala Ser Glu Ala Val Arg Ala Ile Glu Lys Thr Ser Lys Asn Thr Arg
            340                 345                 350

Tyr Thr His Gly His Gly Ser Glu Thr Leu Tyr Leu Ala Pro Gly Gly
        355                 360                 365

Gly Asp Asp Trp Ile Tyr Asp Leu Gly Ile Lys Tyr Ser Phe Thr Ile
370                 375                 380

Glu Leu Arg Asp Thr Gly Thr Tyr Gly Phe Leu Leu Pro Glu Arg Tyr
385                 390                 395                 400

Ile Lys Pro Thr Cys Arg Glu Ala Phe Ala Ala Val Ser Lys Ile Ala
                405                 410                 415

Trp His Val Ile Arg Asn Val
            420

<210> SEQ ID NO 2
<211> LENGTH: 1723
<212> TYPE: DNA
<213> ORGANISM: Homo sapiens

<400> SEQUENCE: 2
gttgtacaga aaattgctgt tgggatgaag ctttgcagcc ttgcagtcct tgtacccatt      60
gttctcttct gtgagcagca tgtcttcgcg tttcagagtg gccaagttct agctgctctt     120
cctagaacct ctaggcaagt tcaagttcta cagaatctta ctacaacata tgagattgtt     180
ctctggcagc cggtaacagc tgaccttatt gtgaagaaaa acaagtcca ttttttttgta    240
aatgcatctg atgtcgacaa tgtgaaagcc catttaaatg tgagcggaat tccatgcagt     300
gtcttgctgg cagacgtgga agatcttatt caacagcaga tttccaacga cacagtcagc     360
ccccgagcct ccgcatcgta ctatgaacag tatcactcac taaatgaaat ctattcttgg     420
atagaattta taactgagag catcctgat atgcttacaa aaatccacat tggatcctca     480
tttgagaagt acccactcta tgttttaaag gtttctggaa agaacaaac agccaaaaat     540
gccatatgga ttgactgtgg aatccatgcc agagaatgga tctctcctgc tttctgcttg     600
tggttcatag ccatataac tcaattctat gggataatag gcaatatac caatctcctg     660
aggcttgtgg atttctatgt tatgccggtg gttaatgtgg acggttatga ctactcatgg     720
aaaaagaatc gaatgtggag aagaaccgt tctttctatg cgaacaatca ttgcatcgga     780
```

```
                                                   -continued
acagacctga ataggaactt tgcttccaaa cactggtgtg aggaaggtgc atccagttcc      840
tcatgctcgg aaacctactg tggactttat cctgagtcag aaccagaagt gaaggcagtg      900
gctagtttct tgagaagaaa tatcaaccag attaaagcat acatcagcat gcattcatac      960
tcccagcata tagtgtttcc atattcctat acacgaagta aaagcaaaga ccatgaggaa     1020
ctgtctctag tagccagtga agcagttcgt gctattgaga aaactagtaa aaataccagg     1080
tatacacatg gccatggctc agaaacctta tacctagctc ctggaggtgg ggacgattgg     1140
atctatgatt tgggcatcaa atattcgttt acaattgaac ttcgagatac gggcacatac     1200
ggattcttgc tgccggagcg ttacatcaaa cccacctgta gagaagcttt tgccgctgtc     1260
tctaaaatag cttggcatgt cattaggaat gtttaatgcc cctgatttta tcattctgct     1320
tccgtatttt aatttactga ttccagcaag accaaatcat tgtatcagat tatttttaag     1380
ttttatccgt agttttgata aaagattttc ctattccttg gttctgtcag agaacctaat     1440
aagtgctact ttgccattaa ggcagactag ggttcatgtc tttttacccct ttaaaaaaaa     1500 ttgtaaaagt ctagttacct acttttttctt tgattttcga cgtttgacta gccatctcaa     1560
gcaactttcg acgtttgact agccatctca agcaagttta atcaaagatc atctcacgct     1620
gatcattgga tcctactcaa caaaaggaag ggtggtcaga agtacattaa agatttctgc     1680
tccaaatttt caataaattt ctgcttgtgc ctttagaaat aca                       1723

<210> SEQ ID NO 3
<211> LENGTH: 18
<212> TYPE: DNA
<213> ORGANISM: Artificial
<220> FEATURE:
<223> OTHER INFORMATION: forward primer

<400> SEQUENCE: 3
cacaccagct ttgctacc                                                     18

<210> SEQ ID NO 4
<211> LENGTH: 21
<212> TYPE: DNA
<213> ORGANISM: Artificial
<220> FEATURE:
<223> OTHER INFORMATION: reverse primer

<400> SEQUENCE: 4
cattttccac tgtttagctc c                                                 21
```